US009200301B2

(12) United States Patent  
Long et al.

(10) Patent No.: US 9,200,301 B2  
(45) Date of Patent: Dec. 1, 2015

(54) MARINE STREPTOMYCES, PYRANOSESQUITERPENE COMPOUND, AS WELL AS PREPARATION METHOD AND APPLICATIONS THEREOF

(75) Inventors: Lijuan Long, Guangzhou (CN); Xinpeng Tian, Guangzhou (CN); Jie Li, Guangzhou (CN); Xiongming Luo, Guangzhou (CN); Zhenxiong Qi, Guangzhou (CN); Tuan Yin, Guangzhou (CN); Hao Yin, Guangzhou (CN); Jian Yang, Guangzhou (CN)

(73) Assignee: SOUTH CHINA SEA INSTITUTE OF OCEANOLOGY, CHINESE ACADEMY OF SCIENCES, Guangzhou (CN)

( * ) Notice: Subject to any disclaimer, the term of this patent is extended or adjusted under 35 U.S.C. 154(b) by 114 days.

(21) Appl. No.: 13/885,853

(22) PCT Filed: Aug. 16, 2012

(86) PCT No.: PCT/CN2012/077068  
§ 371 (c)(1),  
(2), (4) Date: May 16, 2013

(65) Prior Publication Data  
US 2013/0316408 A1 Nov. 28, 2013

(30) Foreign Application Priority Data  
Dec. 30, 2011 (CN) .......................... 2011 1 0460246

(51) Int. Cl.  
*C12P 17/06* (2006.01)  
*C12R 1/465* (2006.01)  
(Continued)

(52) U.S. Cl.  
CPC ................ *C12P 17/06* (2013.01); *A01N 43/16* (2013.01); *A01N 43/90* (2013.01); *A01N 63/00* (2013.01); *A01N 63/02* (2013.01); *C07D 309/32* (2013.01); *C12N 1/20* (2013.01); *C12R 1/465* (2013.01)

(58) Field of Classification Search  
None  
See application file for complete search history.

(56) References Cited

FOREIGN PATENT DOCUMENTS

| CN | 101037656 A | 9/2007 |
|----|-------------|--------|
| CN | 101050209 A | 10/2007 |
| CN | 101688191 A | 3/2010 |

OTHER PUBLICATIONS

Zhu et al., Int. J. Systematic and Evolutionary Microbiol. 61: 2811-2815 (2011).*

(Continued)

*Primary Examiner* — Patricia A Leith  
*Assistant Examiner* — Erin M Bowers  
(74) *Attorney, Agent, or Firm* — Westerman, Hattori, Daniels & Adrian, LLP (57) ABSTRACT

The invention discloses marine *Streptomyces* sp., a Pyranosesquiterpene compound, as well as a preparation method and uses thereof. *Streptomyces* sp. SCSIO 01689 was collected in China Center for Type Culture Collection (CCTCC) (Address: Wuhan University, Wuhan City, China) with the collection number of CCTCC NO: M 2011257 on Jul. 18, 2011. The *Streptomyces* sp. SCSIO 01689 can produce the Pyranosesquiterpene compound with better anti-*Escherichia coli* activity and anti-*Artemia* activity, as well as Cyclo(D)-Pro-(D)-Ile, Cyclo(D)-Pro-(D)-Leu and Cyclo(D)-trans-4-OH-Pro-(D)-Phe with better anti-*Vibrio anguillarum* activity and anti-*Artemia* activity, thereby providing a new way for preparing the Cyclo(D)-Pro-(D)-Ile, the Cyclo(D)-Pro-(D)-Leu and the Cyclo(D)-trans-4-OH-Pro-(D)-Phe. The Pyranosesquiterpene compound can be used for preparing anti-Escherichia coli medicaments and anti-*Artemia* medicaments, as well as preparing condiments as a condiment precursor compound.

3 Claims, 2 Drawing Sheets

(51) Int. Cl.
*A01N 43/16* (2006.01)
*C12N 1/20* (2006.01)
*C07D 309/32* (2006.01)
*A01N 43/90* (2006.01)
*A01N 63/00* (2006.01)
*A01N 63/02* (2006.01)

(56) References Cited

OTHER PUBLICATIONS

Yong-Zhong, Huang et al.: "Research Advances on Secondary Metabolites and Bioactivity of the Marine Sediment-Derived Streptomyces," Nat Prod. RES DEV (2011), 23, pp. 758-766.

Li, Li et al.: "Development in Research of New Antifungal Materials from Microorganism," Institute of Life Science and Technology, (2010) pp. 544-547.

Fdhila, Faouzi, et al.: "DD-Diketopiperazines: Antibiotics Active against Vibrio anguillarum Isolated from Marine Bacteria Associated with Cultures of Pecten maximus," Journal of Natural Products (2003) 66:10.

Lin, Xin et al.: "Biosynthesis of the Sesquiterpene Antibiotic Albaflllavenone in Streptomyces coelicolor. Mechanism and Stereochemistry of the Enzymatic formation of Epi-isozizaene," J. Am. Chem. Soc. (2009), 11 pp. 6332-6333.

Wang, Jian-Hua et al.: "Determination of diketopiperazines of Burkholderia cepacia CF-66 by gas chromatography-mass spectrometry," Anal. Bioanal Chem (2010) 396, pp. 1773-1779.

Delort, Estelle et al.: "Identification and Synthesis of New Volatile Molecules Found in Extracts Obtained from Distinct Parts of Cooked Chicken," Journal of Agriculturla and Food Chemistry (2011) 59, pp. 11752-11763.

Adamczeksi, Madeline et al.: "New and Known Diketopiperazines From the Caribbean Sponge, Calyx CF. PODATYPIA1," Journal of Natural Products (1995) 58:2, pp. 201-208.

Tian, Xin-Peng et al.: "Sciscionella marina gen. nov., sp. nov., a marine actinomycete isolated from a sediment in the northern South China Sea," International Journal of Systematic and Evolutionary Microbiology (2009) 59, pp. 222-228.

Stackebrandt, Erko et al.: "Taxonomic parameters revisited: tarnished gold standards," Microbiology Today (2006) pp. 15-155.

Xiao, Hui et a., "Studies on Pathogens of rotted Gill and rotted Caudal Fins of Seaperch (Lateolabrax japonicus) Fry," China Academic Journal Abstract.

Dong-mei, Gao et al., Study on immune efficacy induced by killed Vibrio anguillarum vaccine on Flounder (Paralichthys olivaceus) China Academic Journal Abstract.

International Search Report for PCT/CN2012/077068 dated Sep. 19, 2012.

* cited by examiner

SEQUENCE LISTING

<160> NUMBER OF SEQ ID NOS: 1

<210> SEQ ID NO 1
<211> LENGTH: 1419
<212> TYPE: DNA
<213> ORGANISM: Streptomyces species
<220> FEATURE:
<221> NAME/KEY: misc_feature
<223> OTHER INFORMATION: SCSIO 01689 strain

<400> SEQUENCE: 1

```
ggctctacca tgcagtcgac gatgaacctc ctccgggagg ggaagagtgg cgaacgggtg      60
agtaacacgt gggcaatctg ccctgcactc tgggataact ccgggaaacc ggagctaata     120
ccggatacga ctctccaggg catcctgggg ggtggaaagc tccggcggtg caggatgagc     180
ccgcggccta tcagctggtt ggtggggtga cggcccacca aggcgacgac gggtagccgg     240
cctgagaggg cgaccggcca cactgggact gagacacggc ccagactcct acgggaggca     300
gcagtgggga atattgcaca atgggcgcaa gcctgatgca gcgacgccgc gtgagggatg     360
acggccttcg ggttgtaaac ctctttcagc agggaagaag cggaagtgac ggtacctgca     420
gaagaagcac cggctaacta cgtgccagca gccgcggtaa tacgtagggt gcgagcgttg     480
tccggaatta ttgggcgtaa agagctcgta ggcggcctgt cgcgtcggat gtgaaagccc     540
ggggcttaac cccgggtctg cattcgatac gggcaggcta gagttcggta ggggagatcg     600
gaattcctgg tgtagcggtg aaatgcgcag atatcaggag gaacaccggt ggcgaaggcg     660
gatctctggg ccgatactga cgctgaggag cgaaagcgtg gggagcgaac aggattagat     720
accctggtag tccacgccgt aaacgttggg cactaggtgt gggcggcatt ccacgtcgtc     780
cgtgccgcag ctaacgcatt aagtgccccg cctggggagt acggccgcaa ggctaaaact     840
caaaggaatt gacgggggcc cgcacaagcg gcggagcatg tggcttaatt cgacgcaacg     900
cgaagaacct taccaaggct tgacatacac cggaaacacg tggagacacg tgccccttg      960 tggtcggtgt acaggtggtg catggctgtc gtcagctcgt gtcgtgagat gttgggttaa    1020
gtcccgcaac gagcgcaacc cttgttctgt gttgccagcg tgcccttcgg ggtgacgggg    1080
actcacagga gactgccggg gtcaactcgg aggaaggtgg ggacgacgtc aagtcatcat    1140
gccccttatg tcttgggctg cacacgtgct acaatggccg gtacaatgag ctgcgatgcc    1200
gcgaggtgga gcgaatctca aaaagccggt ctcagttcgg attggggtct gcaactcgac    1260
cccatgaagt cggagtcgct agtaatcgca gatcagcact gctgcggtga atacgttccc    1320
```

```
gggccttgta cacaccgccc gtcacgtcac gaaagtcggt aacacccgaa gccggtggcc    1380
caaccccttg cgggaggaat cgtcgaaggt ggaccgggg                           1419
```

MARINE STREPTOMYCES, PYRANOSESQUITERPENE COMPOUND, AS WELL AS PREPARATION METHOD AND APPLICATIONS THEREOF

CROSS REFERENCE TO RELATED APPLICATIONS

The present application is a national phase entry under 35 U.S.C. §371 of International Application No. PCT/CN2012/077068, filed Jun. 18, 2012, which claims the benefit of Chinese Patent Application No. 201110460246.3, filed Dec. 30, 2011, the disclosures of which are hereby incorporated herein in their entirety.

FIELD OF THE INVENTION

The invention belongs to the field of industrial microbiology and specifically relates to a *Streptomyces* sp. SCSIO 01689 new species capable of producing a new Pyranosesquiterpene compound with special flavor and strong-activity cyclic dipeptide type compounds, namely Cyclo(D)-Pro-(D)-Ile, Cyclo(D)-Pro-(D)-Leu and Cyclo(D)-trans-4-OH-Pro-(D)-Phe, a method for preparing the Pyranosesquiterpene compound and the strong-activity cyclic dipeptide type compounds, namely the Cyclo(D)-Pro-(D)-Ile, the Cyclo(D)-Pro-(D)-Leu and the Cyclo(D)-trans-4-OH-Pro-(D)-Phe by utilizing the *Streptomyces* sp. SCSIO 01689, as well as the Pyranosesquiterpene compound and uses thereof.

BACKGROUND OF THE INVENTION

*Vibrio anguillarum* is popular pathogenic bacteria of aquaculture animals around the world and can infect salmon, steelhead, eel, *plecoglossus altivelis*, weever, gadidae, turbot, flounder, yellow croaker and the like (Gao Dongmei, Li ham and Wang Qun, Study on immune efficacy induced by killed *Vibrio anguillarum* vaccine on Flounder, Marine Fisheries Research, 2004, 25(1): 486-492). As for part of fish infected with the *Vibrio anguillarum*, local color fading appeared on the body surfaces firstly, fin rays, fin bases and the lower parts of branchial skeletons were engorged and redden, the anus were red and swollen, then the muscle tissues had disseminated or point-like hemorrhage, the body surfaces became black and the fins had ulceration; and when dissection test was performed, obvious yellow viscous ascites was observed, intestinal mucosa tissues became rotten and fell off, and the livers of part of the fish were necrotized (Xiao Hui, Li Jun, Xu Huaishu, et al., Studies on Pathogens of Rotted Gill and Rotted Caudal Fins of Seaperch, Journal of Ocean University of Qingdao, 1999, 29(1):89). The *Vibrio anguillarum* is a serious disease in aquaculture.

Cyclic peptide type compounds, namely Cyclo(D)-Pro-(D)-Ile (compound 2), Cyclo(D)-Pro-(D)-Leu (compound 3) and Cyclo(D)-trans-4-OH-Pro-(D)-Phe (compound 4) are known compounds, the structural formulae are as shown in Formula (II) and the compounds were disclosed in the following documents: document 1, Journal of Natural Products, 2003, 66(10): 1299-1301; document 2, Journal of Natural Products, 1995, 58 (2): 201-208; and document 3, Anal Bioanal Chem, 2010, 396:1773-1779. The Cyclo(D)-Pro-(D)-Ile (compound 2), the Cyclo(D)-Pro-(D)-Leu (compound 3) and the Cyclo(D)-trans-4-OH-Pro-(D)-Phe (compound 4) disclosed in Fdhila F et al., Journal of Natural Products, 2003, 66(10): 1299-1301 had great bactericidal activity against the *Vibrio anguillarum*.

SUMMARY OF THE INVENTION

The first object of the invention is to provide *Streptomyces* sp. SCSIO 01689, which was collected in China Center for Type Culture Collection (CCTCC) (Address: Wuhan University, Wuhan City, China) with the collection number of CCTCC NO: M 2011257 on Jul. 18, 2011.

Figure 1:
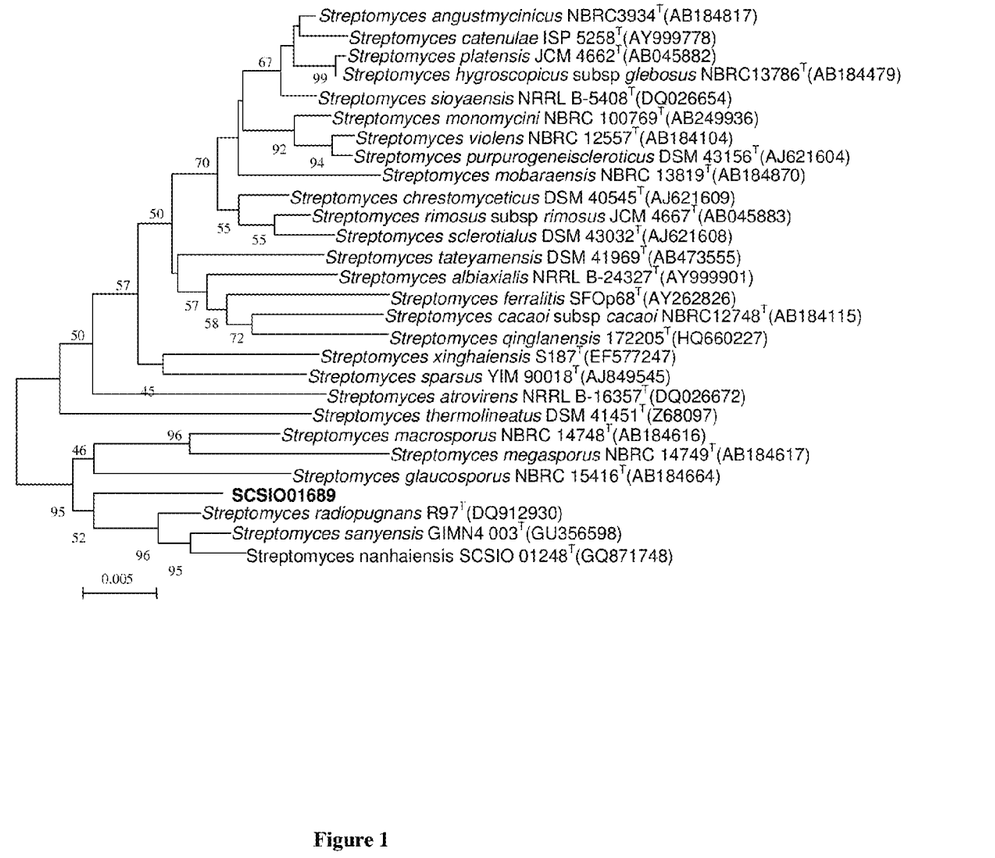
FIG. 1 is a phylogenetic tree of relationship among *Streptomyces* sp. SCSIO 01689 and species with closest kinship, which is reconstructed through a neighbor-joining method based on a 16s rDNA sequence.
Figure 2:
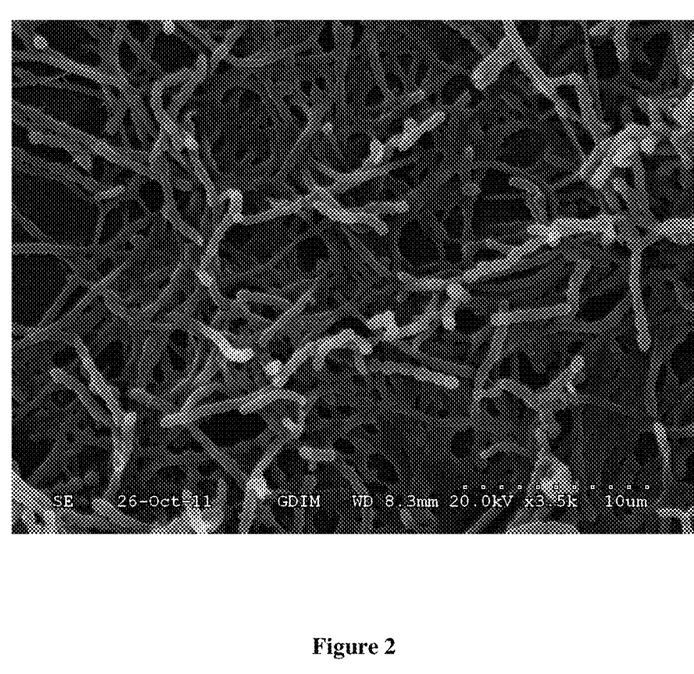
FIG. 2 is a scanning electron micrograph of spore morphology of *Streptomyces* sp. SCSIO 01689.

The *Streptomyces* sp. SCSIO 01689 disclosed by the invention is obtained by separation from submarine sediment 45 m underwater of Sanya Bay (E109° 32', N18° 11') in the northern South China Sea. The conventional PCR (polymerase chain reaction) amplification is performed on 16S rDNA (recombinant deoxyribonucleic acid) of the *Streptomyces* sp. SCSIO 01689, sequencing is performed, and the sequence is as shown in SEQ ID NO. 1. The BLAST analysis is performed on the nucleotide sequence of the 16S rDNA, and the result shows that the similarity between the strain SCSIO 01689 and *Streptomyces sanyensis* is 98.3%, indicating that the strain SCSIO 01689 is *Streptomyces*. As shown in FIG. 1, the phylogenetic relationship between the strain and the *Streptomyces* sp. is clearly disclosed through a neighbor-joining method, showing that the strain belongs to one of the *Streptomyces*. Morphological characteristics and physiological and biochemical analyses are as follows:

The strain SCSIO 01689 belongs to Gram-positive and aerobic actinomycosis, and aerial mycelia are white, branched and differentiated into curled spore chains; and spores are oval (FIG. 2), 1.5-2.0 μm in length and smooth in surfaces. The strain SCSIO 01689 can hydrolyze starch and Tweens 20, 40 and 60, is positive in gelatin liquefaction, milk solidification and peptonization, can decompose cellulose, produce $H_2S$ and hydrolyze Tween 80 and is negative in oxidase and nitrate reduction reaction. The strain SCSIO 01689 is positive in catalase reaction, can produce melanin and is negative in urease reaction. The strain SCSIO 01689 can utilize D-cellobiose, D-galactose, D-glucose, D-maltose, D-mannose, D-raffinose, D-ribose, D-sucrose, D-sorbitol and xylitol, fructose or D-xylose as a sole carbon source and energy source for growth, and can not utilize D-arabinose, D-trehalose, inositol, D-mannitol, L-rhamnose, galactitol and D-lactose for growth. The tolerance ranges of pH, salt concentration and temperature are 6.0-9.5, 0-5% and 10-45° C. respectively. L-DAP is contained in cell walls. Phospholipid components are PG, DPG, PE, PI, PIM and unknown phospholipid PL. The dominant quinones are MK-9($H_6$) and MK-9($H_8$). The main fatty acids are i-C16:0 and ai-C15:0. The molar content of G+C is 71.8(±0.3) %. According to the above morphological, physiological, chemical and other types of analyses, the strain SCSIO 01689 is different from the known proximate strain *Streptomyces sanyensis* GIMN4.003$^T$ in the aspects of growth salt concentration, pH, tolerant temperature range and the like and greatly different in the aspects of utilization of the sole carbon source, starch hydrolysis, gelatin liquefaction, milk solidification and peptonization, antibacterial activity and the like; furthermore, genomic hybridization shows that the hybridization value between the strain SCSIO 01689 and the most similar strain *Streptomyces* sanyensis GIMN4.003$^T$ is 19%, which is far lower than 70% being the intraspecies variation standard (Stackebrandt, E. & Ebers, J. Taxonomic parameters revisited: tarnished gold standards. *Microbiol Today*. (2006). 33, 152-155). Therefore, by comprehensively analyzing multiple items of classified data, the strain is identified as a new species of *Streptomyces*, the strain is named as the *Streptomyces* sp. SCSIO 01689, and the strain was collected in China Center for Type Culture Collection (CCTCC) (Address: Wuhan University, Wuhan City, China) with the collection number of CCTCC NO: M 2011257 on Jul. 18, 2011.

The *Streptomyces* sp. SCSIO 01689 disclosed by the invention has the activity of fat degradation and protein degradation and can produce lipase and proteolytic enzyme, so that the *Streptomyces* sp. SCSIO 01689 disclosed by the invention can be applied to the preparation of the lipase or the proteolytic enzyme and added in aquatic product foodstuff and raw materials for preventing and treating diseases.

The present inventors found that the *Streptomyces* sp. SCSIO 01689 can produce a new Pyranosesquiterpene compound as shown in Formula (I), as well as Cyclo(D)-Pro-(D)-Ile (compound 2), Cyclo(D)-Pro-(D)-Leu (compound 3) and Cyclo(D)-trans-4-OH-Pro-(D)-Phe (compound 4).

Therefore, the *Streptomyces* sp. SCSIO 01689 disclosed by the invention has an application in the preparation of the Pyranosesquiterpene compound as shown in Formula (I), the Cyclo(D)-Pro-(D)-Ile, the Cyclo(D)-Pro-(D)-Leu or the Cyclo(D)-trans-4-OH-Pro-(D)-Phe.

The second object of the invention is to provide a new Pyranosesquiterpene compound, the structure formula of which is as shown in Formula (I):

Formula (I)

The third object of the invention is to provide a preparation method of the Pyranosesquiterpene compound as shown in Formula (I), the Cyclo(D)-Pro-(D)-Ile, the Cyclo(D)-Pro-(D)-Leu or the Cyclo(D)-trans-4-OH-Pro-(D)-Phe, which is characterized in that the Pyranosesquiterpene compound, the Cyclo(D)-Pro-(D)-Ile, the Cyclo(D)-Pro-(D)-Leu or the Cyclo(D)-trans-4-OH-Pro-(D)-Phe is obtained by preparation and separation from a fermentation culture of the *Streptomyces* sp. SCSIO 01689.

Preferably, the Pyranosesquiterpene compound, the Cyclo(D)-Pro-(D)-Ile, the Cyclo(D)-Pro-(D)-Leu or the Cyclo(D)-trans-4-OH-Pro-(D)-Phe is obtained by preparation and separation from the fermentation culture of the *Streptomyces* sp. SCSIO 01689, and the specific steps are as follows:

a) preparing the fermentation culture of the *Streptomyces* sp. SCSIO 01689, extracting fermentation liquid of the fermentation culture by ethyl acetate and distilling and concentrating to remove ethyl acetate and get an extract; and b) performing silica gel column chromatography on the extract, performing gradient elution by using chloroform/acetone as eluent in the volume ratio of 100:0 to 0:100, and collecting fractions, which are respectively Fr.1 and Fr.2 obtained by gradient elution when the chloroform/acetone volume ratio is 95:5 and 60:40; performing gel column chromatography on the fraction Fr.1 to get a crude product, and purifying to get the Pyranosesquiterpene compound; and performing gel column chromatography on the fraction Fr.2 to get a crude product, and purifying to get the Cyclo(D)-Pro-(D)-Ile, the Cyclo(D)-Pro-(D)-Leu and the Cyclo(D)-trans-4-OH-Pro-(D)-Phe.

The fermentation culture of the *Streptomyces* sp. SCSIO 01689 prepared in the step a) is prepared preferably through the following method: inoculating the activated *Streptomyces* sp. SCSIO 01689 into a seed culture medium, culturing at 28° C. and 180 rpm for 3 days to prepare seed liquid, inoculating the seed liquid into a fermentation culture medium according to 5% inoculation amount, and performing shaking culture at 28° C. and 180 rpm for 8 days to prepare the fermentation culture, wherein both formulae of the seed culture medium and the fermentation culture medium are as follows: each liter of each culture medium contains 5 g of starch, 5 g of soybean meal, 2 g of peptone, 20 g of glucose, 2 g of yeast extract, 0.5 g of $K_2HPO_4$, 0.5 g of $MgSO_4.7H_2O$, 30 g of crude sea salt and the balance of water, and the pH is 7.4. The contents of the Pyranosesquiterpene compound and the cyclic dipeptide type compounds, namely the Cyclo(D)-Pro-(D)-Ile, the Cyclo(D)-Pro-(D)-Leu and the Cyclo(D)-trans-4-OH-Pro-(D)-Phe in the fermentation culture of the *Streptomyces* sp. SCSIO prepared by the method are higher.

The purification in the step b) is chromatographic column separation.

It is found in experiments that the Pyranosesquiterpene compound disclosed by the invention has stronger anti-*Escherichia coli* activity, and the MIC (minimal inhibitory concentration) value is 1.58 μg/ml, so that the Pyranosesquiterpene compound can be applied to the preparation of anti-*Escherichia coli* medicaments.

It is found in experiments that the Pyranosesquiterpene compound disclosed by the invention has stronger anti-*Artemia* activity, and the $LC_{50}$ value of the Pyranosesquiterpene compound against *Artemia* larvae is 3.25 μg/ml, so that the Pyranosesquiterpene compound can be applied to the preparation of anti-*Artemia* medicaments.

The structure of the Pyranosesquiterpene compound disclosed by the invention is similar to that of each of unique flavoring elements such as Pyranosesquiterpene (8Z)-8-tetradecen-5-olide, (8E)-8-tetradecen-5-olide and (6E)-6-tetradecen-5-olide contained in cooked chicken (reference: J. Agric. Food Chem. 2011, 59, 11752-11763), so that the Pyranosesquiterpene compound disclosed by the invention can be used as a precursor compound of the above condiments, and can be applied to the preparation of the Pyranosesquiterpene (8Z)-8-tetradecen-5-olide, (8E)-8-tetradecen-5-olide or (6E)-6-tetradecen-5-olide condiment.

It is found in experiments that the Cyclo(D)-Pro-(D)-Ile, the Cyclo(D)-Pro-(D)-Leu and the Cyclo(D)-trans-4-OH-Pro-(D)-Phe have anti-*Artemia* activity, and the LC50 values thereof are 55.67 μg/ml, 87.63 μg/ml and 13.45 μg/ml respectively. Therefore, the Cyclo(D)-Pro-(D)-Ile, the Cyclo(D)-Pro-(D)-Leu and the Cyclo(D)-trans-4-OH-Pro-(D)-Phe can be applied to the preparation of the anti-*Artemia* medicaments.

The *Streptomyces* sp. SCSIO 01689 disclosed by the invention can produce the new Pyranosesquiterpene compound with better anti-*Escherichia coli* activity and anti-*Artemia* activity, as well as the Cyclo(D)-Pro-(D)-Ile, the Cyclo(D)-Pro-(D)-Leu and the Cyclo(D)-trans-4-OH-Pro-(D)-Phe with better anti-*Vibrio anguillarum* activity and anti-*Artemia* activity, thereby providing a new way for preparing the Cyclo (D)-Pro-(D)-Ile, the Cyclo(D)-Pro-(D)-Leu and the Cyclo (D)-trans-4-OH-Pro-(D)-Phe. The Pyranosesquiterpene compound can be used for preparing the anti-*Escherichia coli* medicaments and the anti-*Artemia* medicaments, as well as preparing the condiments as the condiment precursor compound.

The *Streptomyces* sp. SCSIO 01689 disclosed by the invention was collected in China Center for Type Culture Collection (CCTCC) (Address: Wuhan University, Wuhan City, China) with the collection number of CCTCC NO: M 2011257 on Jul. 18, 2011.

DETAILED DESCRIPTION OF EMBODIMENTS

The following embodiments are used for further describing the invention rather than limiting the invention.

Embodiment 1

I. Separation and Identification of *Streptomyces* sp. SCSIO 01689

As for extraction of genome DNA (deoxyribonucleic acid), PCR amplification of 16S rDNA, sequence alignment and an establishment method of a phylogenetic tree, as well as physiological, chemical and morphological identification and the like, involved in the identification of *Streptomyces* sp. SCSIO 01689, please refer to references [Tian, X. P., Zhi, X. Y., Qiu, Y. Q., Zhang, Y. Q., Tang, S. K., Xu, L. H., Zhang, S., Li, W. J. *Sciscionella marina* gen. nov., sp. nov., a marine actinomycete isolated from a sediment in the northern South China Sea. *Int J Syst Evol Microbiol,* 2009, 59(Pt 2): 222-228].

The *Streptomyces* sp. SCSIO 01689 disclosed by the invention is obtained by separation from submarine sediment 45 m underwater of Sanya Bay (E109° 32', N18° 11') in the northern South China Sea. A separation culture medium is a 50% R2A culture medium, each liter of the culture medium contains 0.5 g of peptone, 0.5 g of casein acid hydrolysates, 0.5 g of yeast extract, 0.5 g of glucose, 0.5 g of soluble starch, 0.3 g of $KH_2PO_4$, 0.05 g of $MgSO_4 \cdot 7H_2O$, 15.0 g of agar, 500 ml of natural seawater and 500 ml of distilled water, and the pH is 7.2. The separation culture is performed at 28° C. for 14 days. Therefore, the strain SCSIO 01689 is obtained by separation and purification from submarine sediment.

The genome DNA of the strain SCSIO 01689 is extracted according to the method in the references or the conventional method, conventional PCR amplification is performed on 16S rDNA of the strain SCSIO 01689, sequencing is performed, and the sequence is as shown in SEQ ID NO. 1. The BLAST analysis is performed on the nucleotide sequence of the 16S rDNA, and the result shows that the similarity between the strain SCSIO 01689 and *Streptomyces sanyensis* is 98.3%, indicating that the strain SCSIO 01689 is *Streptomyces*. As shown in FIG. 1, the phylogenetic relationship between the strain and the *Streptomyces* sp. is clearly disclosed through a neighbor-joining method, showing that the strain belongs to one of the *Streptomyces*.

Morphological characteristics and physiological and biochemical analyses are as follows:

The strain SCSIO 01689 belongs to Gram-positive and aerobic actinomycete, and aerial mycelia are white, branched and differentiated into curled spore chains; and the spores are oval (FIG. 2), 1.5-2.0 μm in length and smooth in surfaces. The strain SCSIO 01689 can hydrolyze starch and Tweens 20, 40 and 60, is positive in gelatin liquefaction, milk solidification and peptonization, can decompose cellulose, produce $H_2S$ and hydrolyze Tween 80 and is negative in oxidase and nitrate reduction reaction. The strain SCSIO 01689 is positive in catalase reaction, can produce melanin and is negative in urease reaction. The strain SCSIO 01689 can utilize D-cellobiose, D-galactose, D-glucose, D-maltose, D-mannose, D-raffinose, D-ribose, D-sucrose, D-sorbitol and xylitol, fructose or D-xylose as a sole carbon source and energy source for growth, and can not utilize D-arabinose, D-trehalose, inositol, D-mannitol, L-rhamnose, galactitol and D-lactose for growth. The tolerance ranges of pH, salt concentration and temperature are 6.0-9.5, 0-5% and 10-45° C. respectively. L-DAP is contained in cell walls. Phospholipid components are PG, DPG, PE, PI, PIM and unknown phospholipid PL. The dominant quinones are MK-9($H_6$) and MK-9($H_8$). The main fatty acids are i-C16:0 and ai-C15:0. The molar content of G+C is 71.8(±0.3) %. According to the above morphological, physiological, chemical and other types of analyses, the strain SCSIO 01689 is different from the known *S. sanyensis* GIMN4.003$^T$ in the aspects of growth salt concentration, pH, tolerant temperature range and the like and greatly different in the aspects of utilization of the sole carbon source, starch hydrolysis, gelatin liquefaction, milk solidification and peptonization, antibacterial activity and the like; furthermore, genomic hybridization shows that the hybridization value between the strain SCSIO 01689 and the most similar strain *S. sanyensis* GIMN4.003$^T$ is 19%, which is far lower than 70% being the intraspecies variation standard [Stackebrandt, E. & Ebers, J. Taxonomic parameters revisited: tarnished gold standards. *Microbiol Today.* (2006).33, 152-155.]. Therefore, by synthesizing and analyzing multiple items of classified data, the strain is identified as a new species of (*Streptomyces*), the strain is named as the *Streptomyces* sp. SCSIO 01689, and the strain was collected in China Center for Type Culture Collection (CCTCC) (Address: Wuhan University, Wuhan City, China) with the collection number of CCTCC NO: M 2011257 on Jul. 18, 2011.

Embodiment 2

I. Separation, Preparation and Resolution of Compound

1. Culture Medium

A. The preparation method of each liter of a seed culture medium is as follows: adding 5 g of starch, 5 g of soybean meal, 2 g of peptone, 20 g of glucose, 2 g of yeast extract, 0.5 g of $K_2HPO_4$, 0.5 g of $MgSO_4 \cdot 7H_2O$ and 30 g of crude sea salt into 1 liter of water, and enabling the pH to be 7.4, and sterilizing at 121° C. for 30 min; and B. Preparation of fermentation culture medium: a formula the same as that of the seed culture medium is utilized and sterilizing is performed at 121° C. for 30 min

2. Fermentation

2.1 Seed Culture:

respectively inoculating single colonies of the activated *Streptomyces* sp. SCSIO 01689 on a flat plate of a culture dish into 18 flasks, wherein each flask is a 250 mL culture conical flask containing 50 mL of the seed culture medium; and culturing at 28° C. and 180 r·min$^{-1}$ for 3 days to prepare 900 mL of seed liquid.

2.2 Fermentation Culture:

inoculating the seed liquid into 18 L of the fermentation culture medium (placed in 500 mL culture conical flasks, wherein each flask contains 150 ml of the fermentation culture medium, and the total number of the flasks is 120) according to 5% inoculation amount, performing shaking culture at 28° C. and 180 r·min$^{-1}$ for 8 days to prepare 18 L of fermentation culture.

3. Extraction

The extraction comprises the steps of extracting fermentation liquid of the fermentation culture in the volume of 18 L by ethyl acetate in the volume of 36 L, mixing extraction liquid of ethyl acetate, and performing reduced-pressure distillation and concentration on an ethyl acetate layer to get 13.5 g of extract.

4. Separation and Preparation of Compound

The separation and the preparation of the compound comprise the following steps: performing silica gel (200-300 meshes) normal-temperature column chromatography on the extract, performing gradient elution by using chloroform/acetone as eluent in the volume ratio of 100:0 to 0:100, and collecting fractions, which are respectively recorded as Fr.1 and Fr.2 obtained by gradient elution when the chloroform/acetone volume ratio is 95:5 and 60:40.

The LH-20 gel column chromatography is further performed on the fraction Fr.1 (the fraction obtained by elution when the chloroform/acetone volume ratio is 95:5), the chloroform/acetone in the volume ratio of 1:1 is taken as a mobile phase for elution, then high-pressure liquid chromatography preparation is further performed, a high-performance liquid chromatographic instrument is semi-preparation type Waters 600 (250 mm×10 mm, 5 μm, YMC), the mobile phase is methanol/water with the volume ratio of 85:15, the flow rate is 3 ml/min, and a compound 1 is further obtained (the retention time is 32.4 min)

The LH-20 gel column chromatography is further performed on the fraction Fr.2 (the fraction obtained by elution when the chloroform/acetone volume ratio is 60:40), the chloroform/acetone in the volume ratio of 1:1 is taken as the mobile phase for elution, then the high-pressure liquid chromatography preparation is further performed, the high-performance liquid chromatographic instrument is semi-preparation type Waters 600 (250 mm×10 mm, 5 μm, YMC), and when the mobile phase is methanol/water with the volume ratio of 15:85, the flow rate is 3 ml/min, and a compound 2 is further obtained (the retention time is 27.6 min); and when the mobile phone is methanol/water with the volume ratio of 25:75, the flow rate is 3 ml/min, and a compound 3 (the retention time is 24.4 min) and a compound 4 (the retention time is 31.9 min) are obtained.

5. Resolution of Compound

Through structural analysis, the identification results of the compounds 1, 2, 3 and 4 are as follows:

The compound 1: colorless oily (methanol), UV (methanol): 215, 223.0 nm $^1$H NMR (500 MHz, CD$_3$OD) and $^{13}$C NMR (125 MHz, CD$_3$OD), see Table 1. ESIMS m/z 259.1 [M+Na]$^+$, 237.2 [M+H]$^+$, 473.4 [2M+H]$^+$. From a hydrogen spectrum and a carbon spectrum, we can see that the compound 1 contains 1 methyl [δ$_{14}$ 2.16 (t, J=7.0 Hz, H-16) δ$_C$ 14.4 (q, C-16)], 8 methines [δ$_H$ 2.85 (d, J=6.5 Hz, H-3), δ$_C$30.3 (t, C-3); δ$_H$ 2.29 (dt, J=7.0 6.5 Hz, H-7), δ$_C$ 33.0 (t, C-7); δ$_H$2.30 (dt, J=6.5 5.5 Hz, H-8), δ$_C$38.4 (t, C-8); δ$_H$2.28 (dt, J=11.0 6.0 Hz, H-11), δ$_C$ 30.7 (t, C-11); δ$_H$ 2.18 (m, H-12), δ$_C$ 28.6 (t, C-12); δ$_H$2.18 (m, H-13), δ$_C$26.3 (t, C-13); δ$_H$ 2.18 (m, H-14), δ$_C$ 26.2 (t, C-14); δ$_H$ 2.22 (m, H-15), δ$_C$23.7 (t, C-15)], 5 methylenes [δ$_H$ 6.52 (dd, J=11.0 6.5 Hz, H-4), δ$_C$ 126.6 (d, C-4); δ$_H$ 6.00 (t, J=11.0 6.0 Hz, H-5), δ$_C$ 129.4 (d, C-5); δ$_H$ 4.10 (dd, J=7.0 6.0 Hz, H-6), δ$_C$ 73.4 (d, C-6); δ$_H$ 5.64 (dt, J=15.0 5.5 Hz, H-9), δ$_C$ 137.4 (d, C-9); δ$_H$ 5.45 (dt, J=15.0 11.0 Hz, H-10), δ$_C$ 132.4 (d, C-10)] and 1 quaternary carbon [δ$_C$ 170.1 (s, C-2)]. According to an HMBC (heteronuclear multiple bond coherence) correlation spectrum, we can see that H-15 is correlated with C-13/C-14/C-16, H-13 is correlated with C-11/C-12/C-14/C-15, H-9 is correlated with C-7/C-8/C-10/C-11, and a structure with one monoterpene can be obtained; H-4 is correlated with C-2/C-3/C-5/C-6, and it is speculated that the compound may contain a pyran ring; H-7 is correlated with C-5/C-6/C-8/C-9, and it is speculated that the pyran ring is connected with the monoterpene; and by combining with mass spectrometric data, it is determined that the structure is a new Pyranosesquiterpene compound, the structure of which is as shown in Formula (I):

Formula (I)

Data of the compounds 2-4 is as shown in Tables 2-3, the structures of the compounds 2-4 are identified to be as shown in Formula (II) in combination with the references [Journal of Natural Products, 2003, 66 (10): 1299-1301. Journal of Natural Products 1995, 58 (2): 201-208. Anal Bioanal Chem 2010, 396:1773-1779], and the compounds 2-4 are resolved as known compounds, namely Cyclo(D)-Pro-(D)-Ile (compound 2), Cyclo(D)-Pro-(D)-Leu (compound 3) and Cyclo (D)-trans-4-OH-Pro-(D)-Phe (compound 4).

Formula (II)

TABLE 1

NMR Data Attribution of Hydrogen Spectrum and Carbon Spectrum of Compound 1

| | 化合物1 | |
|---|---|---|
| No. | H | C |
| 2 | | 170.1 s |
| 3 | 2.85 (d, 6.5) | 30.3 t |
| 4 | 6.52 (dd, 11.0, 6.5) | 126.6 d |
| 5 | 6.00 (t, 11.0, 6.0) | 129.4 d |
| 6 | 4.10 (dd, 7.0, 6.0) | 73.4 d |
| 7 | 2.29 (t, 7.0, 6.5) | 33.0 t |
| 8 | 2.30 (dt, 6.5, 5.5) | 38.4 t |
| 9 | 5.64 (dt 15.0, 5.5) | 137.4 d |
| 10 | 5.45 (dt, 15.0, 11.0) | 132.4 d |
| 11 | 2.28 (dt, 11.0, 6.0) | 30.7 t |
| 12 | 2.18 (m) | 28.6 t |
| 13 | 2.18 (m) | 26.3 t |
| 14 | 2.18 (m) | 26.2 t |
| 15 | 2.22 (m) | 23.7 t |
| 16 | 2.16 (t, 7.0) | 14.4 q |

Note:
$^1$H-NMR data is determined at 500 MHz, a coupling constant (Hz) exists in brackets, $^{13}$C-NMR data is determined at 125 MHz, and NMR data is measured in deuterated methanol.

TABLE 2

NMR Data Attribution of Hydrogen Spectrum of Compounds 2-4

| No. | 4<br>H-NMR$^{13}$ | 2<br>H-NMR$^{13}$ | 3<br>H-NMR$^{13}$ |
|---|---|---|---|
| 1 | 6.20 (s) | 6.20 (s) | 6.21 (s) |
| 3 | 3.75 (t, 4.5) | 3.73 (t, 4.5) | 3.78 (4.5) |
| 4 | 2.05 (m), 2.42 (m) | 2.24 (m), 2.40 (m) | 2.05 (m), 2.40 (m) |
| 5 | 1.93 (2H, m) | 1.90 (2H, m) | 1.91 (2H, m) |
| 6 | 3.69 (t, 6.5),<br>4.08 (t, 6.5) | 3.69 (t, 6.5),<br>4.09 (t, 6.5) | 3.69 (t, 6.5),<br>4.09 (t, 6.5) |
| 9 | 3.48 (d, 5.0) | 3.52 (d, 5.0) | 3.50 (d, 6.0) |
| 10 | 2.32 (m) | 2.06 (m) | 1.98 (m) |
| 11 | | 0.99 (d, 7.0) | 1.88 (2H, m) |
| 12 | 7.22 (d, 7.0) | 0.99 (d, 7.0) | 0.93 (t, 7.5) |
| 13 | 7.35 (dd, 7.0, 7.5) | | 1.02 (d, 7.0) |
| 14 | 7.29 (dd, 7.0, 7.5) | | |
| 15 | 7.35 (dd, 7.0, 7.5) | | |
| 16 | 7.22 (d, 7.0) | | |

Note:
$^1$H-NMR data is determined at 500 MHz, a coupling constant (Hz) exists in brackets, and NMR data is measured in deuterated methanol.

TABLE 3

NMR Data Attribution of Carbon Spectrum of Compounds 2-4

| No. | 4<br>C-NMR$^{13}$ | 2<br>C-NMR$^{13}$ | 3<br>C-NMR$^{13}$ |
|---|---|---|---|
| 2. | 169.7 | 169.3 | 169.3 |
| 3. | 63.5 | 63.6 | 62.9 |
| 4. | 29.4 | 29.4 | 29.4 |
| 5. | 22.1 | 22.0 | 22.0 |
| 6. | 45.6 | 45.6 | 45.6 |
| 8. | 165.2 | 165.2 | 165.2 |
| 9. | 57.7 | 58.3 | 58.4 |
| 10 | 38.3 | 33.1 | 24.5 |
| 11 | 135.8 | 17.5 | 39.7 |
| 12 | 129.1 | 19.0 | 11.3 |
| 13 | 129.3 | | 15.3 |
| 14 | 127.6 | | |
| 15 | 129.3 | | |
| 16 | 129.1 | | |

Note:
$^{13}$C-NMR data is determined at 125 MHz, and NMR data is measured in deuterated methanol.

Embodiment 3

Activity Test

1. Enzymolysis Activity Test of Strain

*Streptomyces* sp. SCSIO 01689 is inoculated into various culture media for testing the activities of hydrolytic enzymes, culture is performed at 28° C. for 3-7 days, the existence and the sizes of hydrolysis rings around colonies on the different culture media for testing the hydrolytic enzymes are respectively observed, and then the capability of the strain of producing the corresponding hydrolytic enzymes is specifically judged. The culture media for determining the various hydrolytic enzymes and the test methods are as follows:

The culture medium for gelatin liquefaction test: the culture medium comprises the following components: 5 g of peptone, 20 g of glucose and 200 g of gelatin (heating in boiling water bath for dissolution); the pH is 7.2; and 8-pound sterilization is performed for 30 min for preparation. The culture medium is inoculated onto an inclined plane of a tube for later use; and culture is performed at 28° C. for 3-7 days after inoculation, and the culture medium is placed in a refrigerator at 4° C. for 30 min, and then the liquefaction situation is observed. If the culture medium is liquid, liquefaction is performed; and if the culture medium is still solid, no liquefaction is performed.

The culture medium for proteolytic enzyme test: the culture medium comprises 1 g of $KH_2PO_4$, 0.5 g of $K_2HPO_4$, 15 g of skim milk (Difco 232100), 15 g of agar powder and 1000 ml of distilled water, the sterilization is performed at 121° C. for 15 min, cooling is performed till 55-60° C., and then the mixture is poured onto a flat plate for later use. Bacteria are inoculated onto the flat plate for culturing at 28° C. for 3-7 days to observe the production of a transparent ring, the size of the transparent ring determines the situation of enzyme activity, and no transparent ring proves that no protease exists. The culture medium for amylohydrolysis test: the culture medium comprises 10 g of soluble starch, 0.3 g of $K_2HPO_4$, 1 g of $MgCO_3$, 0.5 g of NaCl, 1 g of $KNO_3$, 20 g of agar and 1000 ml of water; the pH is 7.2-7.4, the sterilization is performed at 121° C. for 15 min, the cooling is performed till 55-60° C., and the mixture is poured onto the flat plate for later use; and the preparation of an iodine solution is performed: 1 g of iodine tablets and 2 g of potassium iodide are dissolved in 300 ml of distilled water, the strain is respectively inoculated onto the starch agar flat plate by adopting a point inoculation method, and the iodine solution is dropwise added around colonies for detection when the growth of the strain is good. If amylase is produced, the transparent ring is formed, and the size of the ring represents the activity of the amylase; and if no amylase is produced, the parts around the colonies turn to blue when meeting with the iodine solution.

The culture medium for esterase hydrolysis test: the culture medium comprises 2.64 g of $(NH_4)_2SO_4$, 2.38 g of $KH_2PO_4$, 5.65 g of $K_2HPO_4$, 1.0 g of $MgSO_4.7H_2O$, 0.0064 g of $CuSO_4.5H_2O$, 0.0011 g of $FeSO_4.7H_2O$, 0.0079 g of $MnCl_2.4H_2O$, 0.0015 g of $ZnSO_47H_2O$ and 20 g of agar, and 10 g of each of Tweens 20, 40 or 80 is added; and the culture medium further comprises 1000 ml of water, the pH is 7.2-7.4, 15-pound sterilization is performed for 30 min, and the flat plate is prepared for later use. The strain is inoculated onto the flat plate by adopting the point inoculation method, and the culture is performed at 28° C. for 3-7 days.

Experimental results: the *Streptomyces* sp. SCSIO 01689 has obvious hydrolysis rings against the Tween 20 and the Tween 40, and the diameter of the hydrolysis rings is 1.5-2 cm; the diameter of the transparent ring against the protease is 1.0-1.3 cm; and no liquefaction phenomenon is produced against the gelatin and no hydrolysis ring exists against the amylase. Therefore, the *Streptomyces* sp. SCSIO 01689 has the activity of lipid degradation and protein degradation and can produce the characteristics of the lipase and the proteolytic enzyme.

2. Activity Test of Compound 2.1 Anti-*Vibrio anguillarum* Activity Test

The experimental method is briefly described as follows: 1. enabling *Vibrio anguillarum* to grow under conventional culture conditions for later use; 2. diluting the tested samples (the compound 1, the compound 2, the compound 3 and the compound 4) to the concentration of 20 mg/mL by taking DMSO (dimethyl sulfoxide) as a solvent, and respectively adding 5 μl of diluted solutions sucked by a gun head, on paper sheets with the diameter of 6 mm; 3. uniformly coating the cultured *Vibrio anguillarum* in a culture dish with the diameter of 10 cm, which contains an LB (Luria-Bertani) culture medium (containing 10 g/L of tryptone, 5 g/L of yeast extract, 10 g/L of sodium chloride, 1.2% of agar powder and 1000 ml of deionized water and having the pH value of 7.4), and culturing at 37° C.; 4. placing the paper sheets with the tested samples on the flat plates in the culture dish and numbering, and observing after 24 h; and 5. prescreening, then diluting by 2, 4, 8 and 16 times, and testing and calculating the MIC values by using the same method.

Screening Results

The samples are preliminarily tested under the situation that each sample is 100 μg/tablet, and the samples are found to have better activities. Then a dilution multiple method is adopted for testing the MIC values (the diameters of the paper sheets are 6 mm, 6-10 mm means weak activity, 10-15 mm means medium activity and 15 mm or more means strong activity). The screening results are as shown in Table 4.

TABLE 4

Analysis Table of Resistances of Compounds 1, 2, 3 and 4 to *Vibrio anguillarum*

| Compounds | MIC (μg/mL) |
|---|---|
| Pyranosesquiterpene compound (compound 1) | >100 |
| Cyclo(D)-Pro-(D)-Ile (compound 2) | 0.05 |
| Cyclo(D)-Pro-(D)-Leu (compound 3) | 0.04 |
| Cyclo(D)-trans-4-OH-Pro-(D)-Phe (compound 4) | 0.07 |

As for the MIC values of the compounds 2, 3 and 4, please refer to Fdhila F et al,. Journal of Natural Products, 2003, 66 (10): 1299-1301.

From Table 4, we can see that the Cyclo(D)-Pro-(D)-Ile (compound 2), the Cyclo(D)-Pro-(D)-Leu (compound 3) and the Cyclo(D)-trans-4-OH-Pro-(D)-Phe (compound 4) have better inhibitory activity against *Vibrio anguillarum*; and as for the new Pyranosesquiterpene compound (compound 1), the MIC value against the *Vibrio anguillarum* is more than 100 μg/mL, and the inhibitory activity is weaker.

2.2 Anti-*Escherichia coli* Activity Test

The experimental method is briefly described as follows: 1. enabling *Escherichia coli* to grow under conventional culture conditions for later use; 2. diluting the tested samples (the compound 1, the compound 2, the compound 3 and the compound 4) to the concentration of 20 mg/mL by taking the DMSO as the solvent, and respectively adding 5 μl of diluted solutions sucked by a gun head, on the paper sheets with the diameters of 6 mm; 3. uniformly coating cultured the *Escherichia coli* into the culture dish with the diameter of 10 cm, which contains an LB culture medium, and culturing at 37° C.; 4. placing the paper sheets with the tested samples on the flat plates in the culture dish and numbering, and observing after 24 h; 5. diluting rifampicin to 0.2 mg/mL by taking DMSO as the solvent and processing the rifampicin in the same way as positive control; and 6. prescreening, then diluting by 2, 4, 8 and 16 times, and testing and calculating the MIC values by using the same method.

Screening Results

The samples are preliminarily tested and compared with the positive control, namely the rifampicin under the situation that each sample is 100 μg/tablet and the rifampicin taken as a standard product is 1 μg/tablet. Then the dilution multiple method is adopted for testing the MIC values (the diameter of each of the paper sheets is 6 mm, 6-10 mm means weak activity, 10-15 mm means medium activity and 15 mm or more means strong activity), and the screening results are as shown in Table 5:

TABLE 5

Anti-*Escherichia coli* Activity Test Table of Compounds 1-4

| Compounds | MIC (μg/mL) |
|---|---|
| Pyranosesquiterpene compound (compound 1) | 1.58 |
| Cyclo (D)-Pro-(D)-Ile (compound 2) | >100 |
| Cyclo (D)-Pro-(D)-Leu (compound 3) | >100 |
| Cyclo (D)-trans-4-OH-Pro-(D)-Phe (compound 4) | >100 |

From Table 5, we can see that the new Pyranosesquiterpene compound (compound 1) has better inhibitory activity against *Escherichia coli*, while the MIC values of the Cyclo (D)-Pro-(D)-Ile (compound 2), the Cyclo(D)-Pro-(D)-Leu (compound 3) and the Cyclo(D)-trans-4-OH-Pro-(D)-Phe (compound 4) against the *Escherichia coli* are more than 100 μg/mL, and the inhibitory activities of them are weaker.

2.3 *Artemia* Larva Lethal Test

The experimental method is briefly described as follows:

Hatching of *Artemia* larvae: placing 100 mg of *Artemia* eggs in a 500 mL beaker, adding 400 mL of artificial sea water, inflating air slowly by using a small inflator pump, hatching at room temperature for 24 h, removing egg shells and the unhatched eggs, and continuously culturing the *Artemia* larvae for 24 h for later use.

The biological lethal method of the *Artemia* larvae is as follows: taking a 96-well cell culture plate according to a Solis improvement method, and adding 2004, of artificial sea water solution containing 10-15 *Artemia* in each well to prepare a test culture plate. The compound 1, the compound 2, the compound 3 or the compound 4 is prepared into a 20 mg/ml sample solution by using DMSO, and then dilution is performed. A blank control group and sample groups of each concentration are respectively provided with three parallel holes, 54, of the sample solvent (DMSO) is added for the blank control group, 54, of the sample solutions of different concentrations are respectively added into the sample groups, and the final concentrations are 500 μg/mL, 50 μg/mL and 5 μg/mL respectively. The culture is performed at room temperature for 24 h, and then the number of dead individuals of the *Artemia* larvae is detected and counted under a binocular dissecting microscope. The biological lethal activity of the *Artemia* larvae is represented by corrected mortality and is calculated according to the following formula:

Corrected mortality=(survival rate of control group−survival rate of treated group)/survival rate of control group×100%

The three concentrations and the corresponding corrected mortalities are input into a computer for respectively calculating $LC_{50}$ and 95% confidence interval thereof.

The screening results are as shown in Table 6.

TABLE 6

Anti-Artemia Activity Test Table of Compounds 1-4

| Compounds | $LC_{50}$ (μg/mL) |
|---|---|
| Pyranosesquiterpene compound (compound 1) | 3.25 |
| Cyclo(D)-Pro-(D)-Ile (compound 2) | 55.67 |

TABLE 6-continued

Anti-Artemia Activity Test Table of Compounds 1-4

| Compounds | $LC_{50}$ (μg/mL) |
|---|---|
| Cyclo(D)-Pro-(D)-Leu (compound 3) | 87.63 |
| Cyclo(D)-trans-4-OH-Pro-(D)-Phe (compound 4) | 13.45 |

From Table 6, we can see that the new Pyranosesquiterpene compound (compound 1), the Cyclo(D)-Pro-(D)-Ile (compound 2), the Cyclo(D)-Pro-(D)-Leu (compound 3) and the Cyclo(D)-trans-4-OH-Pro-(D)-Phe (compound 4) have better lethal *Artemia* activity; and particularly, the $LC_{50}$ of the new Pyranosesquiterpene compound (compound 1) is 3.25 μg/mL, the anti-*Artemia* activity is very good, and the new Pyranosesquiterpene compound (compound 1) can be used for preparing anti-*Artemia* medicaments.

The invention claimed is:

1. A method of preparing a Pyranosesquiterpene compound, Cyclo(D)-Pro-(D)-Ile, Cyclo(D)-Pro-(D)-Leu or Cyclo(D)-trans-4-OH-Pro-(D)-Phe, comprising:
   preparing a fermentation culture of the *Streptomyces* sp. SCSIO 01689, and
   separating the Pyranosesquiterpene compound, Cyclo(D)-Pro-(D)-Ile, Cyclo(D)-Pro-(D)-Leu or Cyclo(D)-trans-4-OH-Pro-(D)-Phe from the fermentation culture of the *Streptomyces* sp. SCSIO 01689,
   wherein the Pyranosesquiterpene compound is represented by the following Formula (I):

Formula (I)

2. The method of claim 1, wherein the separating the Pyranosesquiterpene compound, Cyclo(D)-Pro-(D)-Ile, Cyclo(D)-Pro-(D)-Leu or Cyclo(D)-trans-4-OH-Pro-(D)-Phe from the fermentation culture of the *Streptomyces* sp. SCSIO 01689 comprises:
   extracting a fermentation liquid of the fermentation culture with ethyl acetate;
   distilling and concentrating to remove the ethyl acetate to produce an extract;
   performing silica gel column chromatography on the extract;
   performing a gradient elution on the silica gel column containing said extract by eluting the silica gel column with chloroform:acetone in a volume ratio that begins at 100:0 and ends at 0:100;
   collecting a first fraction Fr.1 from said gradient elution when the chloroform:acetone ratio is 95:5;
   collecting a second fraction Fr.2 from said gradient elution when the chloroform:acetone ratio is 60:40; and
   performing at least one of the following:
      performing gel column chromatography on the fraction Fr.1 to obtain a first crude product, and purifying the first crude product to obtain the Pyranosesquiterpene compound; and
      performing gel column chromatography on the fraction Fr.2 to obtain a second crude product, and purifying the second crude product to obtain the Cyclo(D)-Pro-(D)-Ile, the Cyclo(D)-Pro-(D)-Leu and the Cyclo(D)-trans-4-OH-Pro-(D)-Phe.

3. The method of claim 1, wherein preparing the fermentation culture of the *Streptomyces* sp. SCSIO 01689 comprises:
   inoculating an activated *Streptomyces* sp. SCSIO 01689 into a seed culture medium, culturing at 28° C. and 180 rpm for 3 days to prepare a seed liquid,
   inoculating the seed liquid into a fermentation culture medium according to 5% inoculation amount, and
   performing shaking culture at 28° C. and 180 rpm for 8 days to prepare the fermentation culture,
   wherein both formulae of the seed culture medium and the fermentation culture medium are as follows: each liter of each culture medium contains 5 g of starch, 5 g of soybean meal, 2 g of peptone, 20 g of glucose, 2 g of yeast extract, 0.5 g of $K_2HPO_4$, 0.5 g of $MgSO_4 \cdot 7H_2O$, 30 g of crude sea salt and the balance of water, and the pH is 7.4; and
   wherein the separating the Pyranosesquiterpene compound, Cyclo(D)-Pro-(D)-Ile, Cyclo(D)-Pro-(D)-Leu or Cyclo(D)-trans-4-OH-Pro-(D)-Phe from the fermentation culture of the *Streptomyces* sp. SCSIO 01689 comprises chromatographic column separation.

* * * * *